(12) United States Patent
Park et al.

(10) Patent No.: US 12,239,644 B2
(45) Date of Patent: Mar. 4, 2025

(54) COMPOSITION FOR PREVENTION OR TREATMENT OF MACULAR DEGENERATION

(71) Applicant: KYUNGPOOK NATIONAL UNIVERSITY INDUSTRY-ACADEMIC COOPERATION FOUNDATION, Daegu (KR)

(72) Inventors: Dong Ho Park, Daegu (KR); In Kyu Lee, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 850 days.

(21) Appl. No.: 17/282,547

(22) PCT Filed: Oct. 30, 2019

(86) PCT No.: PCT/KR2019/014500
§ 371 (c)(1),
(2) Date: Apr. 2, 2021

(87) PCT Pub. No.: WO2020/091430
PCT Pub. Date: May 7, 2020

(65) Prior Publication Data
US 2021/0369708 A1    Dec. 2, 2021

(30) Foreign Application Priority Data

Nov. 2, 2018  (KR) .................. 10-2018-0133677
Oct. 30, 2019 (KR) .................. 10-2019-0136771

(51) Int. Cl.
*A61K 31/506*   (2006.01)
*A61P 27/02*    (2006.01)

(52) U.S. Cl.
CPC ............ *A61K 31/506* (2013.01); *A61P 27/02* (2018.01)

(58) Field of Classification Search
CPC .................................................. A61K 31/506
See application file for complete search history.

(56) References Cited

U.S. PATENT DOCUMENTS

| 2005/0182036 A1* | 8/2005 | Kondo ................ A61K 31/401 |
| | | 514/276 |
| 2008/0015144 A1* | 1/2008 | Brownlee ............ A61K 38/26 |
| | | 514/1.9 |
| 2017/0087179 A1* | 3/2017 | Amselem ............ A61K 31/19 |
| 2017/0258791 A1 | 9/2017 | Miyata |

FOREIGN PATENT DOCUMENTS

| KR | 10-1994-0023484 A | 11/1994 |
| KR | 10-2010-0008548 A | 1/2010 |
| KR | 10-2012-0041390 A | 5/2012 |
| WO | WO-2004/012740 A1 | 2/2004 |
| WO | WO-2005/037990 A2 | 4/2005 |
| WO | WO-2015/112831 A1 | 7/2015 |
| WO | WO-2016/031839 A1 | 3/2016 |

OTHER PUBLICATIONS

Cummings et al., "Treatment of neovascular age-related macular degeneration in patients with diabetes," Clin. Ophthalmol. 2(2):369-375 (2008).

International Search Report and Written Opinion mailed Feb. 21, 2020, for PCT International Patent Application No. PCT/KR2019/014500, Park et al., "Composition for Prevention or Treatment of Macular Degeneration," filed Oct. 30, 2019 (8 pages).

Notice of Reasons for Refusal issued May 10, 2022, for Japanese Patent Application No. 2021-518126, Park et al., "Macular degeneration preventive or therapeutic composition," filed Oct. 30, 2019 (English translation) (8 pages).

Notice of Allowance issued on Jul. 20, 2021 for Korean Patent Application No. 10-2019-0136771, Park et al., "Composition for preventing or treating macular degeneration," filed Oct. 30, 2019 (6 pages) (partial English translation).

* cited by examiner

*Primary Examiner* — Kamal A Saeed
*Assistant Examiner* — Karen Cheng
(74) *Attorney, Agent, or Firm* — Clark & Elbing LLP (57) ABSTRACT

The present disclosure pertains to a pharmaceutical composition comprising fursultiamine or a salt thereof for prevention or treatment of macular degeneration. Fursultiamine decreases the upregulated expression of HIF-1α in retinal pigment epithelial cells and suppresses the growth of choroidal vascular endothelial cells. The pharmaceutical composition comprising fursultiamine or salts thereof according to the present disclosure can be used as a therapeutic agent for various neovascular ocular diseases.

5 Claims, 9 Drawing Sheets

Control

Fursultiamine (scale bar: 100μm)

COMPOSITION FOR PREVENTION OR TREATMENT OF MACULAR DEGENERATION

TECHNICAL FIELD

The present disclosure is made with the support of the Ministry of Health and Welfare, Republic of Korea, under Project No. HI16C1501, which was conducted by the Kyungpook National University Hospital in the research program named "Development of Therapeutic Agent for Diabetic Cardiovascular Complications and Drug Efficacy Test System" as a branch of the research project titled "Leading Characterization Research Program", under the research management of the Korean Heath Industry Development Institute, from 1 Apr. 2016 to 31 Mar. 2021.

The present disclosure is also made with the support of the Ministry of Education, Republic of Korea, under Project No. 2017R1D1A1B03027966, which was conducted by the Kyungpook National University Industry-Academic Cooperation Foundation in the research program titled "Evaluation of Regulatory Efficacy on Choroidal Neovascularization and Augmented Vascular Permeability by Controlling microRNA targeting Semaphorin 3A and Angiopoietin-like 4 as a branch of the research project titled "Basic Science Research Program through the National Research Foundation of Korea, from 1 Jun. 2017 to 31 May 2020.

In addition, the present disclosure was conducted by the Kyungpook National University Industry-Academic Cooperation Foundation in the research program titled "Study on Novel Therapeutic Mechanism for Macular Degeneration by Reprogramming Mitochondrial Energy Metabolism and Regulating Inflammatory Activation in Immune Cells", which was supported by Basic Science Research Program for Veteran Researchers" through the National Research Foundation of Korea funded by the Ministry of Education (grant number 2019R1A2C1084371), from 1 Sep. 2019 to 29 Feb. 2024.

This present application claims the benefit of Korean Patent Application No. 10-2018-0133677, filed to the Korean Intellectual Property Office on 2 Nov. 2018, the content of which is herein incorporated by reference in its entirety.

The present disclosure pertains to a composition for prevention or treatment of macular degeneration. More specifically, the present disclosure pertains to a composition comprising fursultiamine or a salt thereof for prevention or treatment of macular degeneration.

BACKGROUND ART

Macular degeneration is an ocular disease characterized by degeneration of the macula lutea, which may result in blurred or no vision in the center of the visual field. Key risk factors of macular degeneration are known to include age, family history, ethnicity, and smoking. In the early stage of macular degeneration, the central vision becomes blurry. With the progression of the disease, the patients develop distorted vision, and experience part or total visual loss later.

Age-related macular degeneration (AMD) is the leading cause of irreversible blindness in people 50 years of age or over. According to epidemiology studies, the incidence of age-related macular degeneration accounts for 1.2% of the population 52-64 years of age in the USA and increases to 20-37% for the population at 75 years of age or over. The incidence is considered to increase with average age.

There are two main types of age-related macular degeneration. One is non-neovascular age-related macular degeneration, called dry AMA, which is the most common in the AMD patients, accounting for 85% of cases. This dry type is characterized by lipid deposits and atrophy of retinal pigment epithelium. The other is neovascular age-related macular degeneration, which is choroidal neovascularization. In the wet form, blood vessels grow up from the choroid behind the retina, tending to leak exudate and fluid. The proliferation of fibrous tissues in the retina leads to blood leakage below the macular, eventually causing irreversible damage to the photoreceptors and severe vision loss.

According to Korean epidemiological survey as of 2010, the incidence of age-related macular degeneration accounts for 2.92% for the early degeneration and 0.19% for the late degeneration. Among the late macular degeneration, non-neovascular macular degeneration amounts to 3.9% and neovascular macular degeneration covers the other cases, revealing that the frequency of neovascular macular degeneration in Korea is very high, compared to other countries.

For treatment of neovascular age-related macular degeneration, photodynamic therapy is used, or an anti-vascular endothelial growth factor (VEGF) medication is intravitreously injected. Mass-scale clinical studies in various institutes revealed better results from intravitreous injection of anti-VEGF medications.

Thus, various anti-VEGF medications have been developed for use in therapy for neovascular AMD. Representative of anti-VEGF medications is ranibizumab (Lucentis®). This anti-angiogenic is reported to be an effective and safe therapy for patients with neovascular age-related macular degeneration and is used widely used over the world.

However, with the frequent recurrence of the lesion, many injections are needed, imparting a significant load to the patient. In spite of many injections, the lesion may not turn into a beneficial condition in some patients.

Meanwhile, VEGF acts also as a potent vasodilator to maintain the relaxation of coronary arteries and the circulation of blood. Thus, the anti-VEGF injection significant may cause significant side effects because most patients with age-related macular degeneration are elderly and at high risk of cardiovascular diseases.

Accordingly, proposed herein is a novel therapeutic composition that brings about effective therapeutic effects on macular degeneration, with a reduction in the risk of side effects.

DETAILED DESCRIPTION OF THE INVENTION

Technical Problem

Intensive and thorough research, conducted by the present inventors, into the development of a therapeutic agent for macular degeneration with a reduced risk of side effects, resulted in the finding that fursultiamine reduces the upregulated expression of HIF-1α in retinal pigment epithelium and suppresses the growth of vascular endothelial cells, leading to the present disclosure.

Accordingly, a purpose of the present disclosure is to provide a pharmaceutical composition for prevention or treatment of macular degeneration.

Another purpose of the present disclosure is to provide a food composition for prevention or treatment of macular degeneration.

Another purpose of the present disclosure is to provide a pharmaceutical composition for prevention or treatment of neovascular ocular disease.

Another purpose of the present disclosure is to provide a food composition for prevention or alleviation of neovascular ocular disease.

Another purpose of the present disclosure is to provide a method for treatment of macular degeneration.

Another purpose of the present disclosure is to provide a method for treatment of neovascular ocular disease.

Technical Solution

An aspect of the present disclosure pertains to a pharmaceutical composition comprising fursultiamine or a salt thereof for prevention or treatment of macular degeneration.

The present inventors intensively studies on the development of a therapeutic agent for macular degeneration with reduced side effects, culminating in the finding that fursultiamine decreases the upregulated expression of HIF-1α in retinal pigment epithelial cells and suppresses the growth of choroidal vascular endothelial cells.

Fursultiamine (thiamine tetrahydrofurfuryl disulfide, TTFD), is an active form of vitamin Bi used to treat thiamine deficiency. Chemically, it is a disulfide derivative of thiamine, with better cellular uptake than vitamin Bi. Physiologically, its phosphate derivatives including ca-carboxylase are known to treat vitamin Bi deficiency or neural dysfunction associated with metabolic disorder, myocardial dysfunction, etc.

Age, family history, ethnicity, and smoking are common risk factors of macular degeneration. Among them, aging is the leading cause of macular degeneration. In macular degeneration, there is a progressive accumulation of drusen (buildup of extracellular proteins and lipids) between the retinal pigment epithelium and the underlying choroid.

Severity of AMD (age-related macular degeneration) that worse over time is divided into early, intermediate, and late types, partially based on the degree (size and number) of drusen.

According to an embodiment of the present disclosure, the macular degeneration is age-related macular degeneration (AMD).

According to another embodiment of the present disclosure, the macular degeneration is late age-related macular degeneration (late AMD).

In late AMD, enough retinal occurs that, in addition to drusen, people will also begin to experience symptomatic central vision loss. Late AMD is further divided into dry and wet AMD based on the types of damage. Dry AMD is characterized by geographic atrophy and non-neovascular AMD while wet AMD is neovascular AMD with abnormal blood vessel growth in the choriocapillaris.

In another embodiment of the present disclosure, the macular degeneration may be neovascular age-related macular degeneration (neovascular AMD) or non-neovascular age-related macular degeneration (non-neovascular AMD).

In another embodiment of the present disclosure, the macular degeneration is neovascular age-related macular degeneration.

According to an embodiment of the present disclosure, the pharmaceutical composition of the present disclosure may be administered in an effective amount of 100 mg/60 kg/day to 240 mg/60 kg/day as a dose of fursultiamine or a salt thereof alone.

The salt is preferably an acid addition salt formed with a free acid.

The free acid may be an organic acid and/or inorganic acid.

Examples of the organic acid include, but are not limited to, citric acid, acetic acid, lactic acid, tartaric acid, maleic acid, fumaric acid, formic acid, propionic acid, oxalic acid, trifluoroacetic acid, benzoic acid, gluconic acid, metasulfonic acid, glycolic acid, succinic acid, 4-toluene sulfonic acid, glutamic acid, and aspartic acid.

The inorganic acid may be chloric acid, bromic acid, sulfuric acid, and phosphoric acid, but without limitations thereto.

The pharmaceutical composition of the present disclosure may comprise a pharmaceutically acceptable carrier in addition to fursultiamine So long as it is typically available for medication formulations, any pharmaceutically acceptable carrier may be used in the present disclosure. Examples include lactose, dextrose, sucrose, sorbitol, mannitol, starch, acasia rubber, calcium phosphate, alginate, gelatin, calcium silicate, microcrystalline cellulose, polyvinyl pyrrolidone, cellulose, water, syrup, methyl cellulose, methylhydroxy benzoate, hydroxypropylbenzoate, talcum, magnesium stearate and mineral oil, but are not limited thereto.

In addition to the ingredients, the pharmaceutical composition of the present disclosure may further comprise a lubricant, a humectant, a sweetener, a flavorant, an emulsifier, a suspending agent, a preservative, etc. With respect to suitable details of pharmaceutically acceptable carriers and formulations, reference may made to *Remington's Pharmaceutical Sciences* (19$^{th}$ ed., 1995).

The pharmaceutical composition of the present disclosure may be administered orally or parenterally.

For parenteral administration, intravenous injection, subcutaneous injection, intramuscular injection, intraperitoneal injection, transdermal injection, intraocular injection, or topical ophthalmic administration may be carried out.

Examples of the topical ophthalmic administration include direct intraocular injection or administration via periocular, retroorbital, subretinal, central retinal, parafovea, subconjunctival, intravitreous, intracameral, or suprachoroidal routes.

The pharmaceutical composition of the present disclosure may be administered with the aid of an injection device.

A suitable dose of the pharmaceutical composition of the present disclosure may vary depending on various factors including formulation types, administration modalities, the patient's age, body weight, sex, severity of diseases, diet, administration time, administration route, excretion rate, and sensitivity. Generally, a practitioner can determine and prescribe a dose effective for the purpose of treatment.

The pharmaceutical composition according to the present disclosure may be formulated using pharmaceutically acceptable carriers and/or excipients according to methods which can be easily carried out by those skilled in the art. The composition may be manufactured as a unit dosage form or incorporated into a multiple dose container. In this regard, the formulation may be a solution, suspension, or emulsion in an oil or aqueous medium, or a paste, an extract, a powder, a granule, a tablet, or a capsule, and may further comprise a dispersant or a stabilizer.

Another aspect of the present disclosure provides a food composition comprising fursultiamine or a salt thereof for prevention or alleviation of macular degeneration.

For a food composition, the composition of the present disclosure may be formulated into powders, granules, tablets, capsules, or beverages.

In the present disclosure, the food may be candies, beverages, gums, teas, vitamin complexes, or health supplement foods.

The food composition of the present disclosure may comprise an ingredient typically used for food preparations as well as fursultiamine or a salt thereof as an active ingredient. For example, the food composition may comprise a protein, a carbohydrate, a lipid, a nutrient, a seasoning, and a flavorant. Examples of the carbohydrate include typical sugars, such as monosaccharides, e.g., glucose, fructose, etc.; disaccharides, e.g., maltose, sucrose, etc.; oligosaccharides; and polysaccharides, e.g., dextrin, cyclodextrin, and sugar alcohols such as xylitol, sorbitol, erythritol, etc.

The flavorant available in the present disclosure may be natural (such as taumatin, stevia extract (e.g., levaudioside A, glycyrrhizin, etc.)) or synthetic (such as saccharin, aspartame, etc.).

When prepared into a drink production, the food composition of the present disclosure may further comprise citric acid, high-fructose corn syrup, sugar, glucose, acetic acid, malic acid, fruit juice, an Eucommia ulmoides Oliver extract, a jujube extract, a licorice extract, and etc.

Another aspect of the present disclosure provides a pharmaceutical composition comprising fursultiamine or a salt thereof for prevention or treatment of a neovascular ocular disease.

The pharmaceutical composition for prevention or treatment of neovascular ocular disease and the food composition for prevention or alleviation of neovascular ocular disease have fursultiamine or a salt thereof in common with the pharmaceutical composition for prevention or treatment of macular degeneration. Therefore, the common descriptions therebetween are omitted in order to avoid undue redundancy leading to the complexity of this specification.

As used herein, "neovascular ocular disease" refers to a disease occurring in the eyeball in association with pathological neovascularization and is intended to encompass, for example, corneal neovascularization, retinal neovascularization, choroidal neovascularization, intraocular neovascularization, neovascular glaucoma, proliferative diabetic retinopathy, neovascular macular degeneration, and retinopathy of prematurity.

Another aspect of the present disclosure provides a method for treatment of macular degeneration, the method comprising a step of administering to a subject in need thereof a pharmaceutical composition comprising fursultiamine or a salt thereof.

Another aspect of the present disclosure provides a method for treatment of a neovascular ocular disease, the method comprising a step of administering to a subject in need thereof a pharmaceutical composition comprising fursultiamine or a salt thereof.

As used herein, the term "administration" means providing a substance of interest to a subject by any suitable method. So long as it guides an active ingredient to a target tissue, any typical route, whether orally or parenterally, may be taken for administering the pharmaceutical composition of the present disclosure. In addition, the pharmaceutical composition of the present disclosure may be administered using any device capable of delivering an active ingredient to a target cell or organ.

As used herein, the term "subject" is intended to encompass, but not limited to, humans, monkeys, cattle, horses, sheep, pigs, chickens, turkeys, quails, cats, dogs, mice, rabbits, and guinea pigs, with preference for mammals and more preference for humans.

Advantageous Effects

Features and advantages of the present disclosure are as follows:
(a) the present disclosure pertains to a pharmaceutical composition comprising fursultiamine or a salt thereof for prevention or treatment of macular degeneration;
(b) fursultiamine reduces the increased expression of HIF-1α in retinal pigment epithelial cells and suppresses the growth of choroids vascular endothelial cells; and
(c) the pharmaceutical composition comprising fursultiamine or a salt thereof according to the present disclosure can be used as a therapeutic agent for various neovascular ocular diseases.

BRIEF DESCRIPTION OF THE DRAWINGS

FIG. 2b is a graph showing quantitative analysis of the choroid sprouting distance in FIG. 2a.

BEST MODE FOR INVENTION

The present disclosure pertains to a pharmaceutical composition comprising fursultiamine or a salt thereof for prevention or treatment of macular degeneration.

MODE FOR CARRYING OUT THE INVENTION

A better understanding of the present disclosure will be obtained from the following examples which are set forth to illustrate, but should not be construed to limit, the present illustrative Example 1: Inhibitory Effect of Fursultiamine on Neovascularization—HIF-1α Downregulation Neovascular age-related macular degeneration is characterized by choroidal neovascularization. In the retina or choroid, hypoxia increases the expression of HIF-1α (hypoxia inducible factor 1 alpha) which, in turn, promotes VEGF to induce neovascularization in the choroid. This choroidal neovascularization results in a loss of vision.

In the present disclosure, the thiamine derivative fursultiamine was assayed for inhibitory activity against HIF-1α and preventive effect on choroidal neovascularization. To this end, in-vitro tests were conducted with ARPE-19 (Adult Retinal Pigment Epithelial cell line-19).

ARPE-19 cells are seeded into 60-mm dishes and incubated overnight to adhere to the dishes. On the next day, the cells were treated with fursultiamine-HCl (Toronto research chemical, F865230) or a vehicle (dimethyl sulfoxide (DMSO), Sigma-Aldrich) at the specific concentrations of 0 μM, 20 μM, 50 μM, and 100 μM. After one hour, the cells were exposed to 1% oxygen condition in a hypoxic chamber (INVIVO$_2$ 400, Baker). After hypoxic exposure for 4-6 hours, the cells were lysed with a protein lysis buffer and protein isolation from the lysate was conducted.

Protein concentrations were measured using a BCA protein assay kit (Pierce BCA protein assay kit, Thermo Fisher Scientific). Samples with the same protein amounts were mixed with 4× loading buffer and boiled to denature the proteins into the primary structure before being loaded on SDS-PAGE gel. After electrophoresis, the proteins were transferred onto a PVDF membrane. The membrane was incubated overnight at 4° C. with a dilution of an anti-HIF-1α antibody (Novus, NB100-479) in 5% BSA (bovine serum albumin) solution.

On the next day, the membrane was incubated with a HRP (horseradish peroxidase)-conjugated secondary antibody, followed by reaction with ECL (enhanced chemiluminescence) reagent to induce chemiluminescence. The western blots were scanned with a chemiluminescence image analyzer (GE Healthcare, LAS-4000) to give an image exhibiting luminescence intensities depending on protein amounts. As a loading control, β-tubulin showed that the same protein amounts were loaded.

Figure 1:
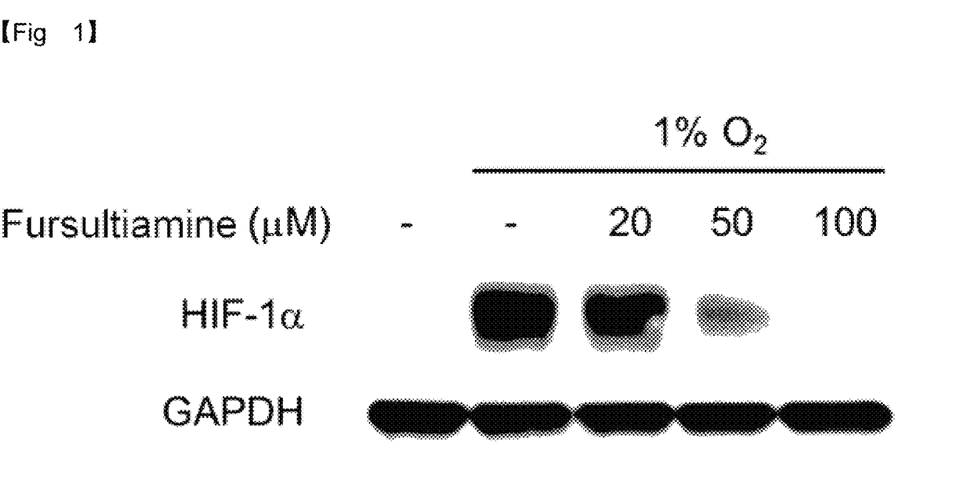
FIG. 1 shows the inhibitory effect of fursultiamine on the expression of HIF-1α, which is induced by hypoxia, in ARPE-19 cells, as analyzed by immunoblotting.

As a result, the expression of HIF-1α which was upregulated in the hypoxic condition (1% oxygen) was reduced by treatment with fursultiamine (FIG. 1).

Example 2: Inhibitory Effect of Fursultiamine on Neovascularization—Suppression of Choroidal Vascular Endothelial Cell Growth Effects of fursultiamine on the growth of choroidal vascular endothelial cells were evaluated by the ex vivo mouse choroid sprouting assay for age-related macular degeneration.

The eyeball was resected from C57BL/6J mice (Jackson Laboratory) at 3 or 4 weeks of age and the choroid/sclera was separated therefrom and sectioned into a size of 1 mm×1 mm. After being thawed on ice, Matrigel (Becton Dickinson, BD matrigel) in a liquid state was added in an amount of 300 μl to each well of 24-well plates and one of the cut choroid/sclera segments was seeded in the Matrigel in each well. Then, Matrigel was solidified for 10 min in a 37° C. incubator before adding 500 μl of an EGM medium (Lonza, Endothelial Growth Medium) to each well.

Subsequently, the growth of vascular endothelial cells was induced in a 37° C. incubator. The medium was exchanged every two days with a fresh one containing 20 μM or 50 μM fursultiamine-HCl. The growth of vascular endothelial cells from the choroid was monitored from the day of seeding the choroid/sclera and observed on day 3 to 5. The sprouting distances were measured at a total of 4 sites using the ImageJ software and averaged. Statistical analyses were performed with the Prism program, with statistical significance defined as p<0.05.

Figure 2A:
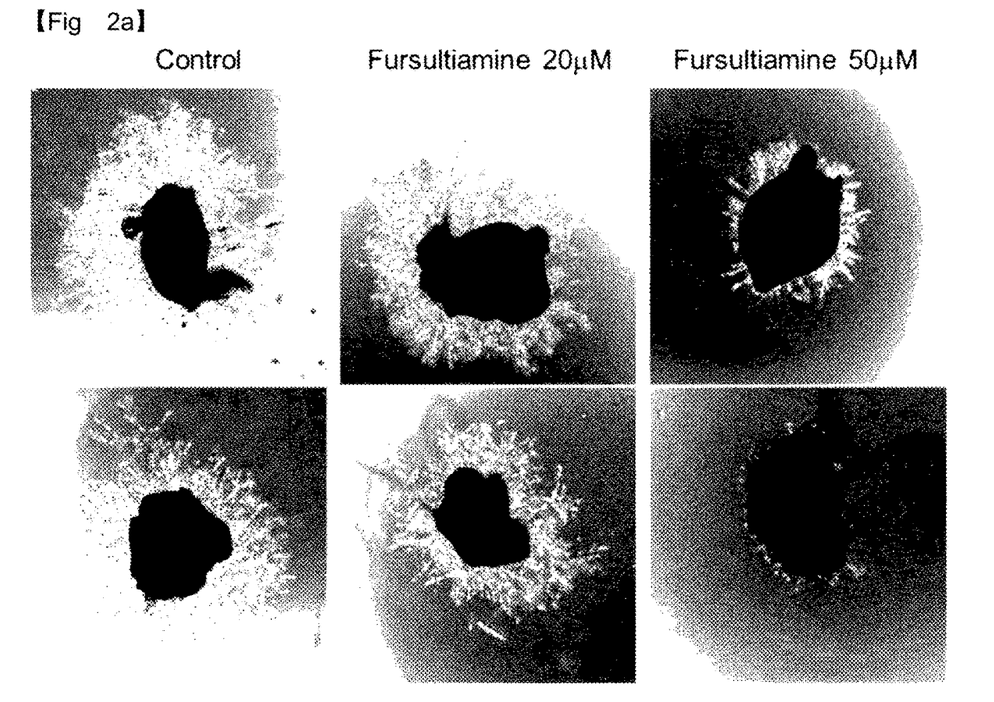
FIG. 2a shows results of the choroid sprouting assay in which the sprouting region was reduced by fursultiamine (magnification ×40)
Figure 2B:
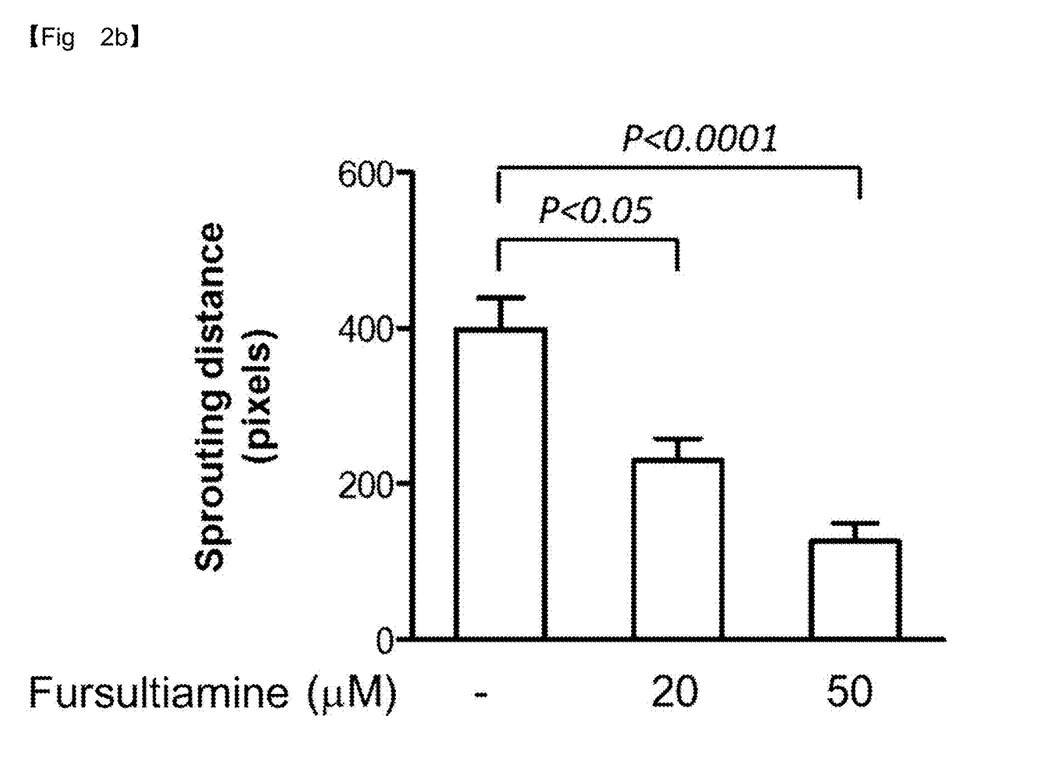

As a result, it was observed that the growth of vascular endothelial cells was inhibited by fursultiamine (FIGS. 2a-2b and Table 1).

TABLE 1

| | Fursultiamine (uM) | | |
| --- | --- | --- | --- |
| | 0 | 20 | 50 |
| Sprouting range (pixels) | 398.417 ± 40.827 | 229.926 ± 28.348 | 126.713 ± 22.810 |

Example 3: Inhibitory Effect of Fursultiamine on VEGF Secretion

ARPE-19 cells were seeded into 60-mm dishes and incubated overnight to adhere to the dishes. On the next day, the medium was replaced with serum-free medium. The cells were treated with fursultiamine-HCl (Toronto research chemical, F865230) or a vehicle (DMSO, Sigma-Aldrich) at the specific concentrations of 0 μM, 50 μM, and 100 μM and then exposed to 1% oxygen condition in a hypoxic chamber (INVIVO$_2$ 400, Baker). After hypoxic exposure for 4-6 hours, the cells were lysed with a protein lysis buffer and protein isolation from the lysate was conducted.

After 12 hours later, the medium was recovered and secreted levels of VEGF in the medium were measured using human VEGF enzyme linked immunoassay (ELISA) (R&D systems). Quantitation methods and concentration calculations were conducted according to the manufacturer's manual. Statistical analyses were performed using the Prism program, with statistical significance defined as p<0.05.

Figure 3:
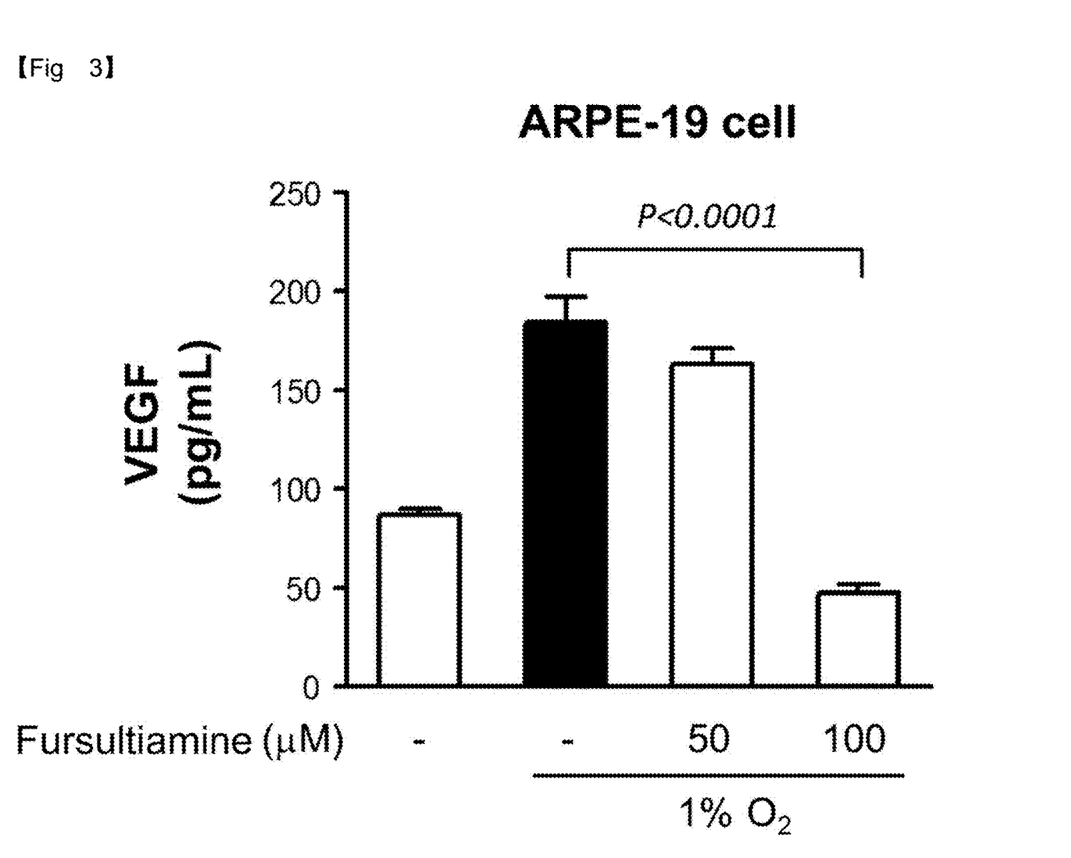
FIG. 3 is a graph showing the inhibitory activity of fursultiamine against the hypoxia-induced upregulation of VEGF secretion in ARPE-19 cells.

As a result, it was observed that the VEGF secretion which was increased in the hypoxic condition (1% oxygen) was suppressed by treatment with fursultiamine (FIG. 3 and Table 2).

TABLE 2

| | Vehicle | 1 | 2 | 3 |
| --- | --- | --- | --- | --- |
| Oxygen condition | 21% O$_2$ | 1% O$_2$ | 1% O$_2$ | 1% O$_2$ |
| Fursultiamine (μM) | 0 | 0 | 50 | 100 |
| VEGF (pg/mL) | 86.6 ± 3.2 | 184.2 ± 12.7 | 163.4 ± 7.4 | 47.4 ± 4.6 |

Example 4: Comparison of Grade of Vascular Leakage Through Fluorescein Angiography For use in assessing the therapeutic potential of fursultiamine in AMD, macular degeneration animal models in which retinopathy was induced by laser was constructed from C57BL/6J mice at 7-8 weeks of age. Ten mice were used for each of fursultiamine-administered and control groups. Fursultiamine was orally administered at a dose of 50 mg/kg for 8 days from one day before laser irradiation to one week after laser irradiation. To the control, sterile distilled water used as a solvent was administered.

The mice were anesthetized with Avertin (Sigma-Aldrich) and administered a mydriatic to induce dilation of the pupil. An argon laser (OcuLight GL, IRIDEX) was projected to both eyes to form four laser spots in each eyeball.

After one week, the mice were anesthetized and intraperitoneally injected with fluorescein (AK-FLUOR 10%, Akorn). Using MICRON IV Basic System (Phoenix Research Labs), retina base and fluoresceine images were captured.

Images for vascular leakage were obtained within 3 minutes (early phase) and about 7 minutes (late phase) after intraperitoneal injection of fluorescein to monitor fluorescence size and intensity between the two time points.

Hyperfluorescence with increasing size and intensity was scored as 2B; hyperfluorescence with constant size but increasing intensity was scored as 2A; hyperfluorescence with differences in none of size and intensity was scored as 1; and faint fluorescence with no spots was scored as 0. More spots scored as 2B accounted for higher neovascular leakages. Statistical analyses were performed using the Prism program, with statistical significance defined as p<0.05.

Figure 4A:
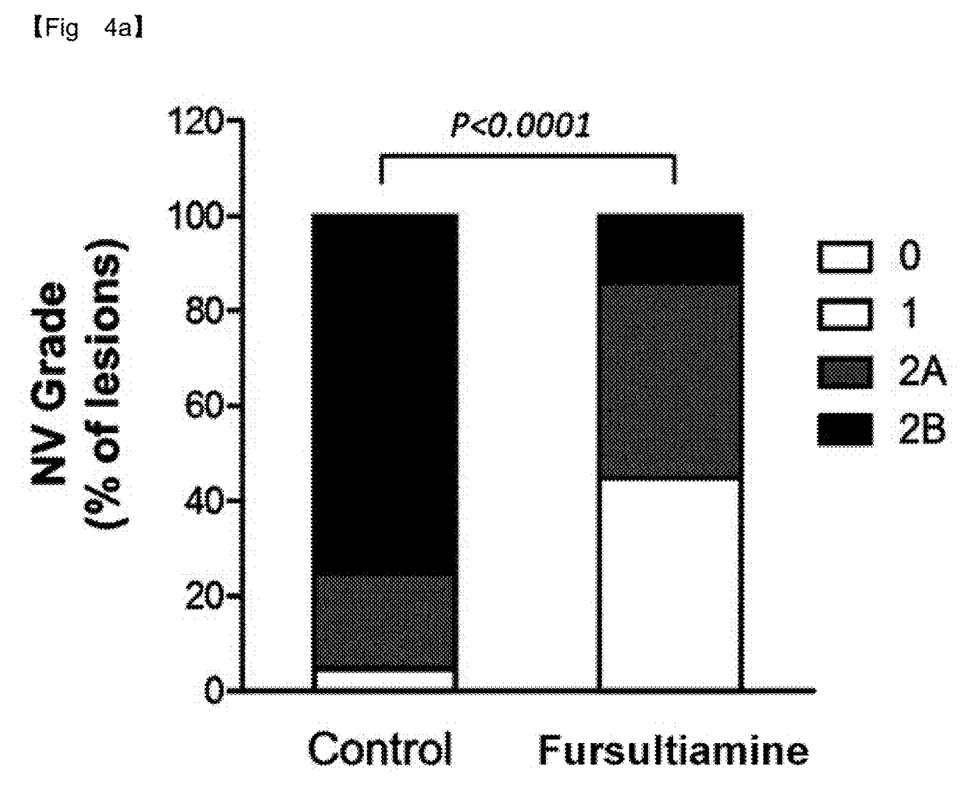
FIGS. 4a-4b shows comparison of vascular leakage in laser-induced choroid neovascularization (CNV) models through fluorescein angiography, revealing that fursultiamine reduces vascular leakage. 0: no laser spots, 1: no changes in size and intensity between early and late phases, 2A: a change only in intensity between early and late phases, 2B: changes in both intensity and size between early and later phases.
Figure 4B:
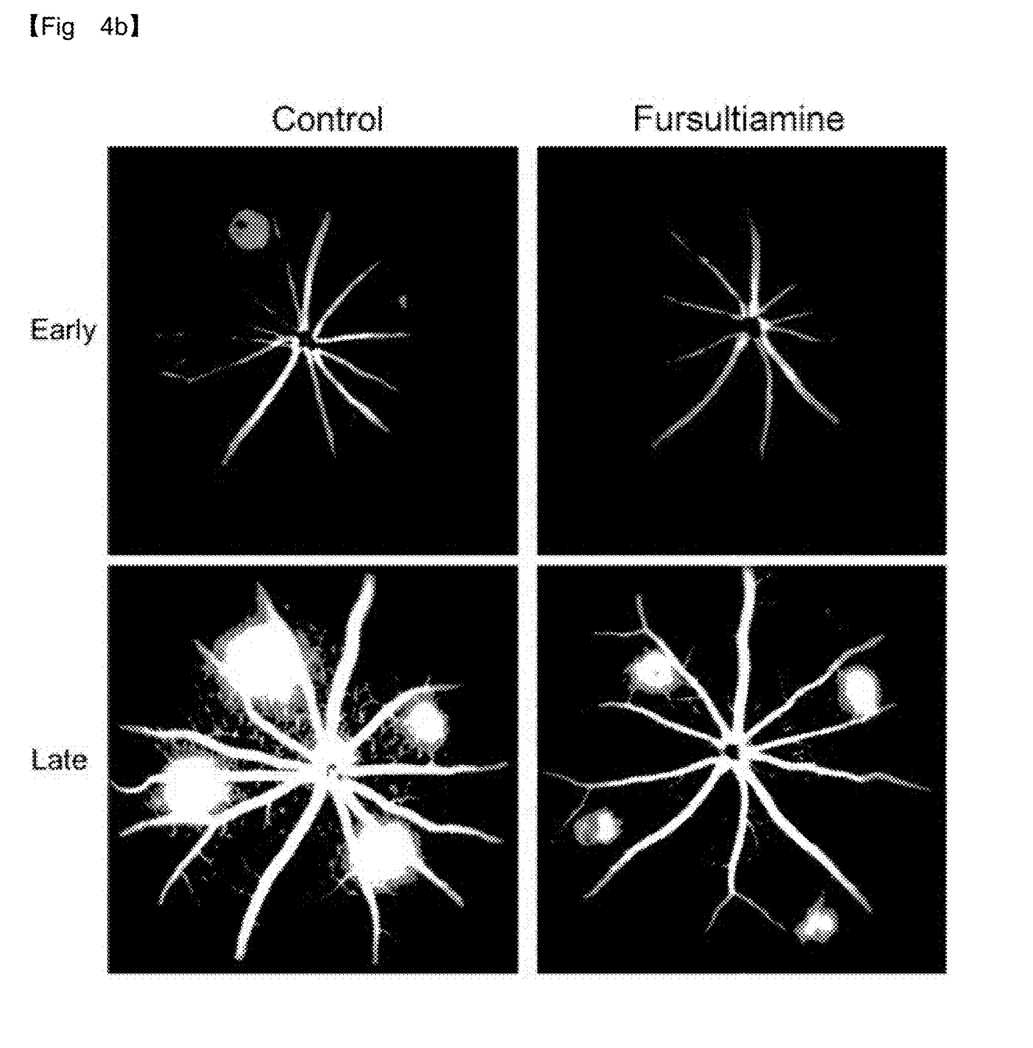

As a result, the vascular leakage for the late phase was decreased in the fursultiamine-treated choroidal retinopathy model, demonstrating that fursultiamine decreases vascular leakage (FIGS. 4a-4b).

Example 5: Size of Choroidal Neovascularization (CNV) Lesion in Laser-Induced CNV Model after Treatment with Fursultiamine In order to construct laser-induced CNV models, C57BL/6J mice at 7-8 weeks of age were anesthetized with Avertin (Sigma-Aldrich) and administered a mydriatic to induce dilation of the pupil, followed by projecting an argon laser (OcuLight GL, IRIDEX) to both eyes to form four laser spots in each eyeball. Ten mice were used for each of fursultiamine-administered and control groups. Fursultiamine was orally administered at a dose of 50 mg/kg for 8 days from one day before laser irradiation to one week after laser irradiation. To the control, sterile distilled water used as a solvent was administered.

One week after laser irradiation, the mice were anesthetized and subjected to fluorescein angiography. For histochemical staining, the eyes were enucleated and fixed in 4% paraformaldehyde (4% PFA, EMS) for 30 min. After removal of the cornea and lens, retinas were separated from the underlying choroid. The separated choroid was incubated for 1 hour in a blocking buffer (0.2% bovine serum albumin, 5% normal goat serum, 0.5% Triton X-100) to which a dilution of an antibody (Isolectin IB4-Alexa Fluor 488, Invitrogen) against isolectin, which is one of vascular markers, in a blocking buffer was then added. After reaction, the choroid was spread flatly and loaded with a mount solution (Mountant, Thermo Scientific), followed by applying a cover glass thereto for stabilization.

On the next day, images were captured at ×100 magnification under a confocal microscope (LSM800, Zeiss). Sizes of laser spots were quantitated using ImageJ program. Statistical analyses were performed using the Prism program, with statistical significance defined as p<0.05.

Figure 5:
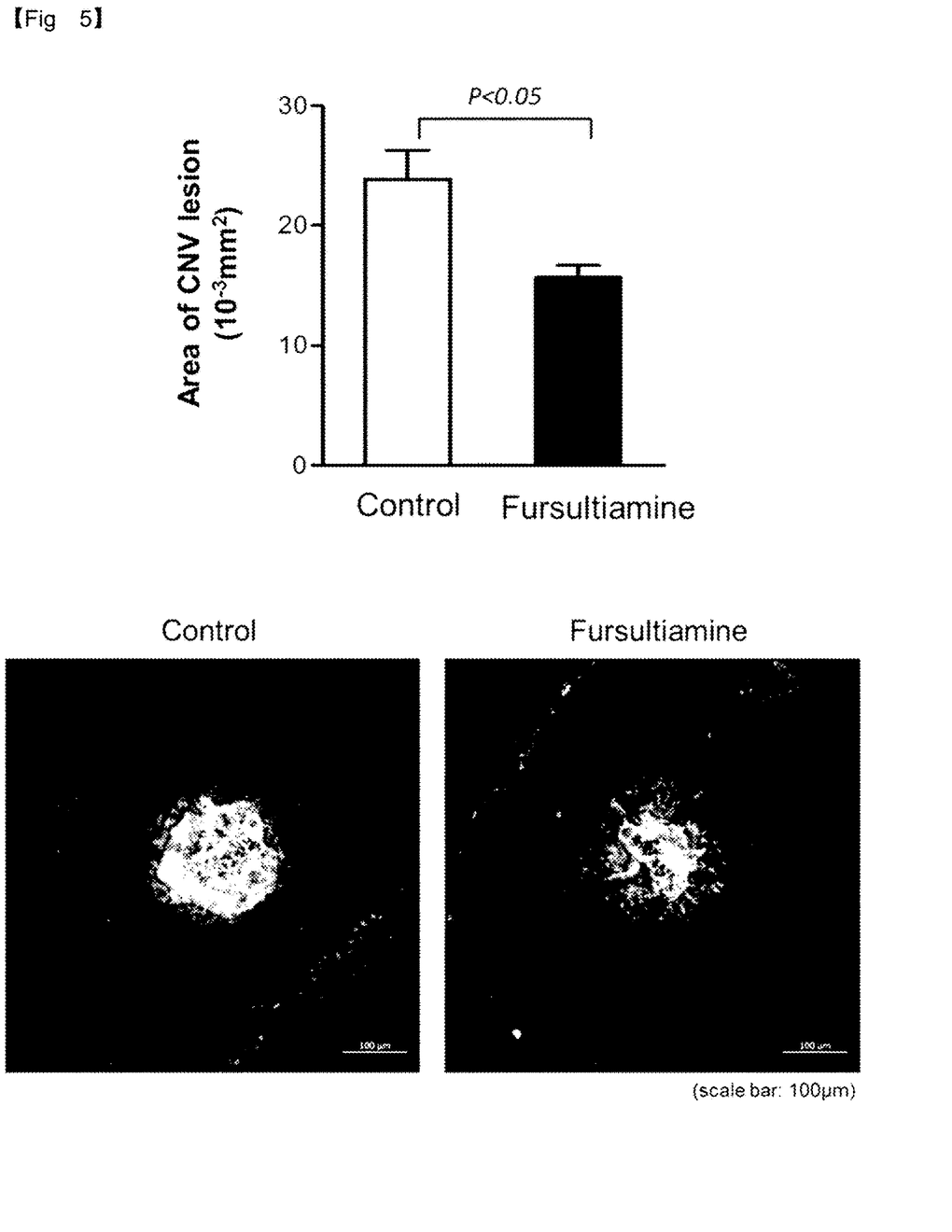
FIG. 5 shows the reduction of CNV lesion sizes by fursultiamine in laser-induced CNV models. Scale bar: 100 μm.

As a result, fursultiamine reduced CNV lesion sizes (FIG. 5 and Table 3).

TABLE 3

| — | Control | Fursultiamine administered |
|---|---|---|
| Fursultiamine (mg/kg) | 0 | 50 |
| Lesion size ($10^{-3} mm^2$) | 23.9 ± 2.4 | 15.7 ± 1.0 |

Example 6: Fursultiamine-Mediated Reprogramming of Mitochondrial Metabolism Recovery in Retinal Pigment Epithelium Inflammation is known to be a leading pathological mechanism in neovascular age-related macular degeneration. Thus, examination was made to see whether fursultiamine treatment reprograms mitochondrial metabolism and thus inhibits inflammation. Because a change in mitochondrial metabolism may cause or aggravate inflammation, fursultiamine was expected to find applications in preventing or treating inflammatory neovascular ocular diseases when reprogramming mitochondrial metabolism.

To be specific, ARPE-19 cells were seeded onto 96-well XF plates, with the exchange of a fresh medium every two days. On day 5 after cell seeding, the cells were treated with 10 μg/ml LPS (lipopolysaccharides, Sigma-Aldrich) and then with 50 μM fursultiamine on day 6. On day 7, the medium was exchanged with an XF medium (Seahorse XF DMEM medium, Agilent) and the plates were left for 30 min at 37° C. in a non-$CO_2$ incubator.

In order to assess mitochondrial spare capacity, the following mitochondrial electron transport inhibitors and respiratory uncouplers were used in corresponding steps: oligomycin (2 μM), FCCP (0.5 μM), rotenone (2 μM), and antimycin A (2 μM).

The oxygen consumption rate (OCR) was measured using an XFe96 analyzer (Agilent) according to the manufacturer's manual.

Figure 6A:
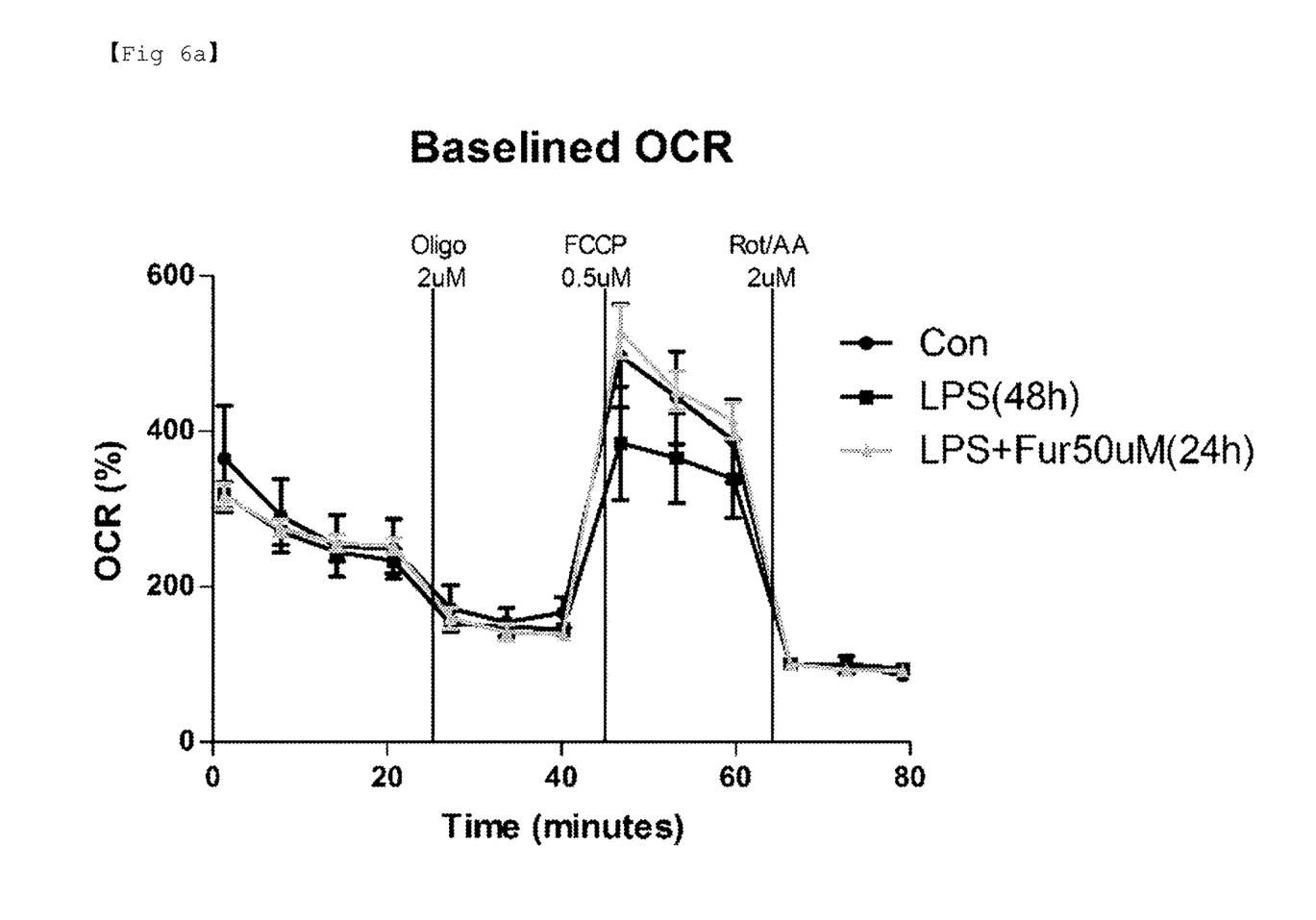
FIG. 6a is a plot of oxygen consumption with time in ARPE-19 cells, showing changes in mitochondrial energy metabolism.
Figure 6B:
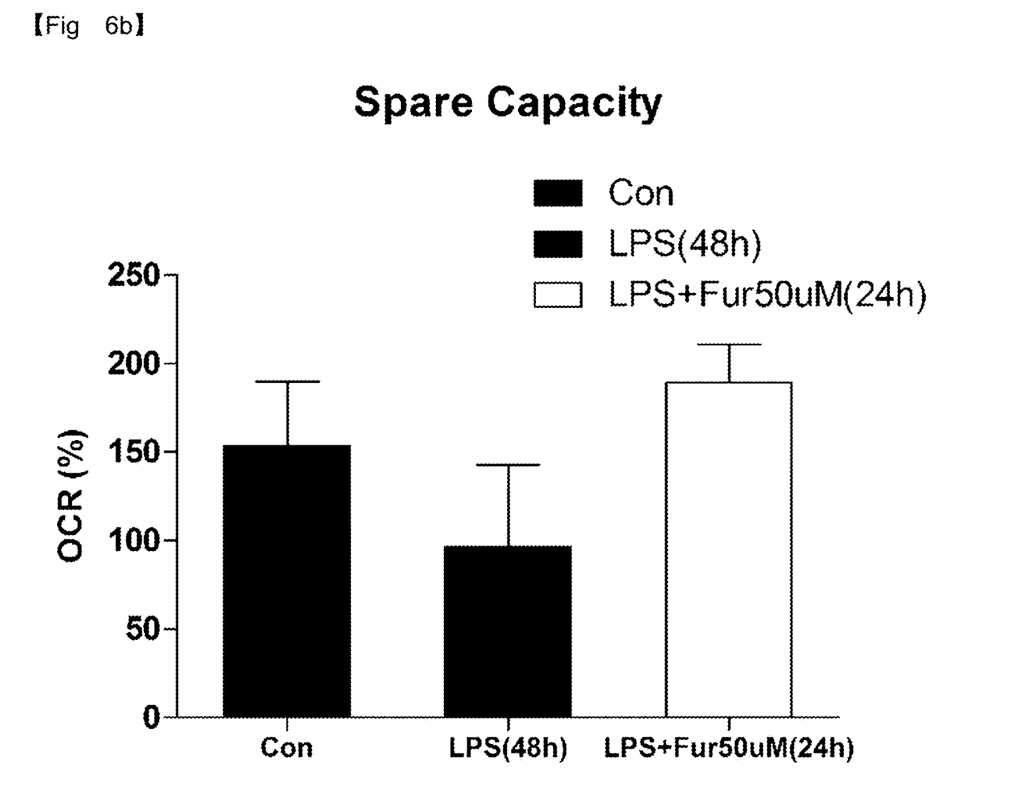
FIG. 6b is a graph of spare capacity, showing that fursultiamine elicits a recovery from the LPS-induced decrease of mitochondrial metabolism.

As a result, fursultiamine treatment enhanced the mitochondrial spare capacity decreased by LPS. These data imply that fursultiamine reprograms mitochondrial energy metabolism and suppresses inflammation (FIGS. 6a-6b and Table 4).

TABLE 4

| | Con | LPS (48 h) | LPS + Fur 50 uM (24 h) |
|---|---|---|---|
| LPS (ug/ml) | — | 10 | 10 |
| fursultiamine (uM) | — | — | 50 |
| OCR (%) | 153.614 ± 36.221 | 96.3486 ± 46.440 | 189.438 ± 21.392 |

Taken together, the data thus obtained indicate that fursultiamine has inhibitory activity against the pathological mechanism of neovascular age-related macular degeneration and a composition comprising fursultiamine is expected to exhibit preventive and therapeutic effects on macular degeneration.

INDUSTRIAL APPLICABILITY

The present disclosure pertains to a composition for prevention or treatment of macular degeneration. More specifically, the present disclosure pertains to a composition comprising fursultiamine or a salt thereof for prevention or treatment of macular degeneration.

The invention claimed is:

1. A method for alleviating, preventing, or treating of macular degeneration in a subject, the method consisting of:
    administering to the subject a pharmaceutical composition, wherein the pharmaceutical composition consists of fursultiamine or a salt thereof as the sole active ingredient for alleviating, preventing, or treating macular degeneration, and a pharmaceutically acceptable carrier or excipient.

2. The method of claim 1, wherein the macular degeneration is age-related macular degeneration.

3. The method of claim 2, wherein the macular degeneration is late age-related macular degeneration (late AMD).

4. The method of claim 2, wherein the macular degeneration is neovascular age-related macular degeneration (neovascular AMD).

5. The method of claim 1, wherein the pharmaceutical composition is administered via an intraocular, periocular, retroorbital, subretinal, central retinal, parafovea, subconjunctival, intravitreous, intracameral, or suprachoroidal route.

* * * * *

UNITED STATES PATENT AND TRADEMARK OFFICE
CERTIFICATE OF CORRECTION

PATENT NO. : 12,239,644 B2
APPLICATION NO. : 17/282547
DATED : March 4, 2025
INVENTOR(S) : Dong Ho Park et al.

Page 1 of 1

It is certified that error appears in the above-identified patent and that said Letters Patent is hereby corrected as shown below:

In the Claims

Column 10, Claim 1, Line 60, replace "alleviating, preventing, or treating of" with --alleviating, preventing, or treating--.

Signed and Sealed this
First Day of July, 2025

Coke Morgan Stewart
*Acting Director of the United States Patent and Trademark Office*